(12) United States Patent
Babichenko et al.

(10) Patent No.: US 7,995,203 B2
(45) Date of Patent: Aug. 9, 2011

(54) METHOD FOR ON-SITE DRUG DETECTION IN ILLICIT DRUG SAMPLES

(75) Inventors: Sergey Babichenko, Tallinn (EE); Tatjana Ivkina, Ontario (CA); Larisa Poryvkina, Tallinn (EE); Vitaly Sominksky, Ontario (CA)

(73) Assignee: Nartest AS, Tallinn (EE)

( * ) Notice: Subject to any disclaimer, the term of this patent is extended or adjusted under 35 U.S.C. 154(b) by 345 days.

(21) Appl. No.: 12/438,597

(22) PCT Filed: Oct. 3, 2006

(86) PCT No.: PCT/EP2006/066974
§ 371 (c)(1),
(2), (4) Date: Feb. 24, 2009

(87) PCT Pub. No.: WO2008/040386
PCT Pub. Date: Apr. 10, 2008

(65) Prior Publication Data
US 2009/0321659 A1 Dec. 31, 2009

(51) Int. Cl.
*G01J 3/30* (2006.01)

(52) U.S. Cl. ........................................... 356/317

(58) Field of Classification Search .................. 356/317; 436/172
See application file for complete search history.

(56) References Cited

U.S. PATENT DOCUMENTS
5,206,179 A * 4/1993 Ramsey .................. 436/537
* cited by examiner

*Primary Examiner* — Tarifur Chowdhury
*Assistant Examiner* — Abdullahi Nur
(74) *Attorney, Agent, or Firm* — Ladas & Parry LLP (57) ABSTRACT

The invention is intended for illicit drug detection, preferably to Cocaine detection in street samples containing in addition to Cocaine also adulterants and/or diluents (also denominated as cutting agents) used for increasing the quantity of the product and/or for disguising the existence of Cocaine. The invention provides preparing of the liquid street sample, taking an aliquot of said sample, its analysis with help of SFS (Spectral Fluorescence Signatures) technology, fixing the result of analysis as a reference value, the subsequent acidification of the liquid sample, taking an aliquot of the acidified liquid sample and its analysis with help of SFS technology, fixing the result of analysis and comparing said result with the reference value. The result of comparison enables to differentiate between Cocaine Base and Cocaine hydrochloride in the street sample.

9 Claims, 9 Drawing Sheets

METHOD FOR ON-SITE DRUG DETECTION IN ILLICIT DRUG SAMPLES

FIELD OF THE INVENTION

This invention relates to the field of illicit drug detection, preferably to Cocaine detection in street samples. In the sense of the present invention, a street sample is a product containing in addition to Cocaine also adulterants and/or diluents (also denominated as cutting agents) used for increasing the quantity of the product and/or for disguising the existence of Cocaine. More particularly the invention relates to a method based on fluorescence in solution and specifically on the Spectral Fluorescence Signatures (SFS) technology, enabling to increase sensitivity of Cocaine detection in the illicit drug samples and allowing differentiation between Cocaine hydrochloride and Cocaine base.

BACKGROUND OF THE INVENTION

A system and a method for on-site drug detection and quantification based on the Spectral Fluorescence Signatures (SFS) technology are disclosed in WO2005111586. The system of this invention consists of an ultraviolet-visible light source, a condenser/filter assembly with filter drive, an excitation monochromator with diffraction grating drive, a reference photo-detector, a cell assembly for liquid, solid and powder samples, an absorption photo-detector, an emission monochromator with diffraction grating drive, and an emission photo-detector. A microcontroller unit is provided for device controlling, data processing, and communication with an external computer via different link types. The detection and quantification of illicit drugs in the analyzed sample are provided by measuring simultaneously the emission spectra of fluorescence at every step of excitation wavelength in selected and fixed excitation, emission and absorption spectral windows in a way to cover specific excitation, emission fluorescence and absorption spectral ranges of all major drugs, adulterants and diluents; and processing the united result in a computer system based on combination of preliminary prepared spectral library and specialized software consisting of identification, interaction verification and automatic calibration modules.

A system and a method of analysis of street samples disclosed in WO2005111586 are limited in detection by the concentration of the substances of interest, in particular Cocaine, at that the specific patterns in SFS structure caused by said substances are not recognized by the expert system due to too low their concentration and interfering influence of adulterants and diluents. Additionally to that the cited invention does not provide reliable means to differentiate between Cocaine hydrochloride and Cocaine base due to the same shapes of SFS caused by both forms of cocaine in water.

The need for a technical solution, which increases the selectivity of on-site analysis related to Cocaine detection in a mixture with cutting agents (adulterants and diluents) and allows differentiation between Cocaine hydrochloride and Cocaine base, is mandated by the legal requirements in illicit drug distribution prevention. The current sentencing structure for Cocaine offenses (United States Sentencing Commission. Guidelines Manual. 2004) is the result of the Anti-Drug Abuse Act of 1986. It established mandatory minimum penalties for persons convicted of trafficking in a variety of controlled substances. The 1986 Act pegged the mandatory minimums to specific quantities of drugs distributed. The quantities triggering the Act's mandatory minimum penalties are differed for various drugs and in some cases for different forms of the same drug. Cocaine base, commonly referred to as crack Cocaine, has been treated differently than Cocaine hydrochloride, commonly referred to as powder Cocaine. The Act established what has come to be known as a 100-to-1 quantity ratio between the two forms of Cocaine. It takes one hundred times as much of powder Cocaine to trigger the same mandatory penalties as for a given amount of crack. Congress also distinguished crack Cocaine from both powder Cocaine and other controlled substances in the Anti-Drug Abuse Act of 1988 by creating a mandatory minimum penalty for simple possession of crack Cocaine. This is the only federal mandatory minimum for a first offense of simple possession of a controlled substance. Under this law, possession of more than five grams of crack Cocaine is punishable by a minimum of five years in prison. Simple possession of any quantity of any other substance—including powder Cocaine—by first-time offenders is a misdemeanor offense punishable by no more than one year in prison.

The cited documents illustrate necessity to detect and differentiate Cocaine hydrochloride and Cocaine base and to provide reliable and selective detection of two forms of Cocaine to fight effectively against this illegal drugs trafficking and abuse.

SUMMARY OF INVENTION

Resulting from the drawbacks of the known technical solution, the first objective of the present invention is to provide a method for on-site drug detection in illicit drug samples using SFS analysis enabling reliable differentiation of Cocaine hydrochloride and Cocaine base in a sample.

Another objective of the present invention is to increase the sensitivity of SFS analysis for Cocaine base detection in the mixtures with cutting agents.

For achieving the above objectives, the suggested method for on-site drug detection in illicit drug samples bases on the analysis performed by the Spectral Fluorescence Signatures (SFS) technology and provides executing of the following steps:

preparing an aliquot liquid sample of a street sample for analysis;

introducing the aliquot liquid sample into the measuring cell of an SFS device;

providing the first measurement of SFS of the aliquot liquid sample;

fixing the result of the first measurement of SFS of the aliquot liquid sample as a reference value;

preparing an acidified aliquot liquid sample after the first measurement;

providing the measurement of SFS of the acidified aliquot liquid sample after passing the time limit necessary for dissolving of Cocaine base;

comparing the reference value and the result of the measurement of SFS of the acidified aliquot liquid sample, and considering lack of any cocaine in the street sample proved if the reference value is zero and the result of the measurement of SFS of the acidified aliquot liquid sample is the same; or considering the existence of Cocaine base in the street sample proved if the result of the measurement of SFS of the acidified aliquot liquid sample exceeds the reference value; or considering lacking of Cocaine base and the existence of Cocaine hydrochloride in the street sample proved if the result of the measurement of SFS of the acidified aliquot liquid sample is below the reference value or equals to the reference value, and the reference value differs form zero.

The preferred time limit provided for dissolving of Cocaine base is at least 3 minutes.

DETAILED DESCRIPTION OF THE INVENTION

According to the present invention, the first step of the method is preparing the liquid sample for analysis. For this purpose the dry sample for analysis (sampled amount of powder or crushed pill) taken by sampling tool (e.g. spatula), is transferred into purified water, and water with powder is mixed to assist dilution of the powder in water. After that, an aliquot (part) of prepared liquid sample is taken and introduced into the measuring cell of the device according to WO2005111586 and SFS of the aliquot of liquid sample is measured accordingly. Upon acquisition of the SFS, the expert system of the device provides the detection of the substance of interest in the sample.

Figure 1:
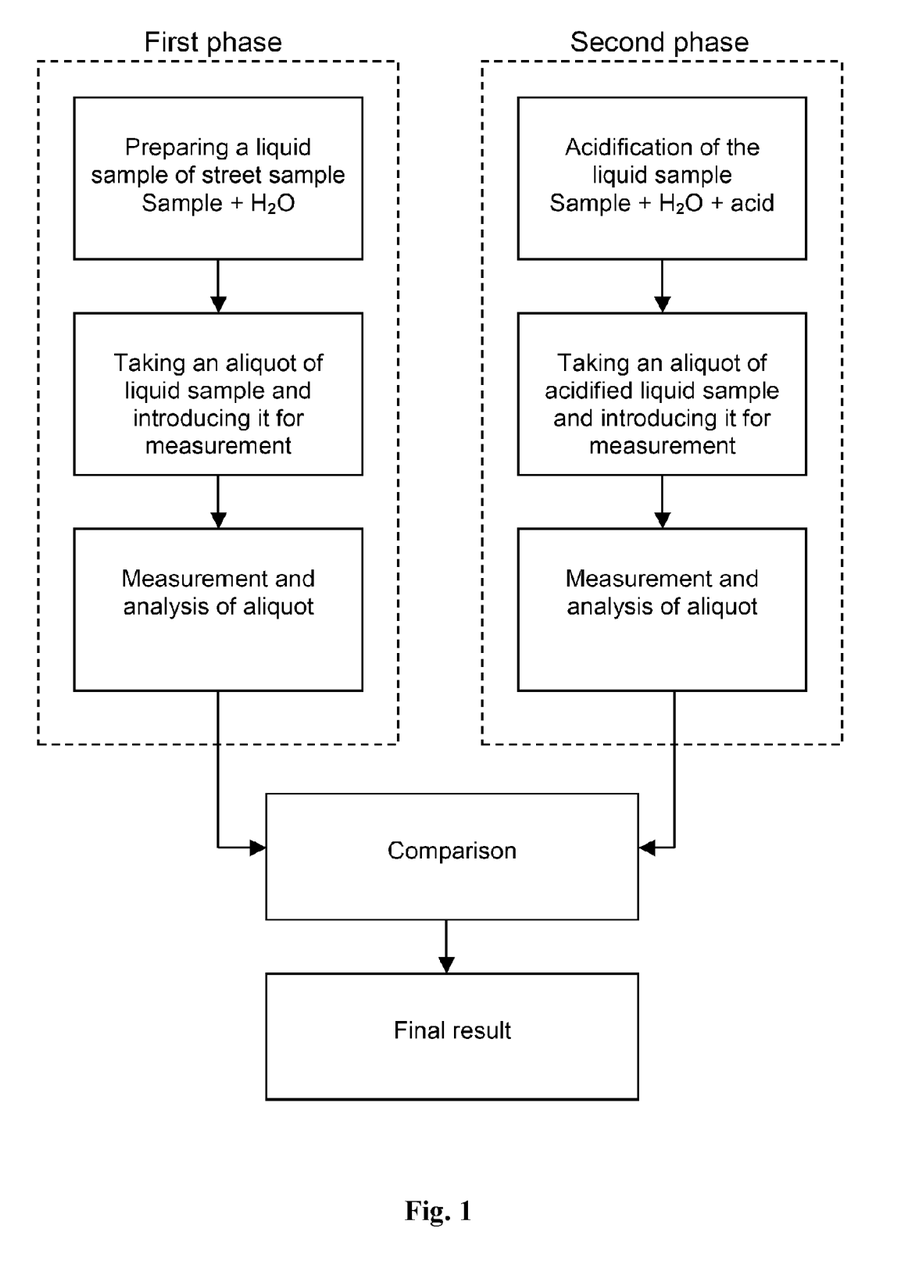
FIG. 1: The flow chart of two-phase procedure of a sample analysis for Cocaine hydrochloride and Cocaine base

The second phase of analysis according to the present invention includes additional treatment of remainder of the liquid sample, its re-measurement with the same device and analysis with expert system (FIG. 1). The second phase is required and performed at following conditions.

1. If no substance of interest, namely Cocaine has been reported by the expert system upon completion of the first phase of analysis, such result can be due to two reasons:
   a) there is no Cocaine in the sample at all;
   b) there is Cocaine in the sample at such concentration that its fluorescence is too low for detection or is influenced by adulterants and diluents hampering the detection of Cocaine by expert system;

Such uncertainty does not allow making the final conclusion about the street sample content.

2. If cocaine detection has been reported at the first phase of analysis, then differentiation between Cocaine base and Cocaine hydrochloride is required.

To solve the problems remained after completing the first phase of analysis, the second phase of analysis procedure is performed (FIG. 1.) which is based on combined influence of two factors.

The first one is that the solubility of Cocaine hydrochloride in water is much higher than the solubility of Cocaine base. Indeed, Cocaine hydrochloride is quickly dissolved in water due to its high water solubility (2-2.5 g/ml) but Cocaine base cannot be dissolved in concentrations higher than 0.0017-0.0014 g/ml. (The Merck Index. 13th edition. 2001). Due to that a taken for analysis dry sample of Cocaine base cannot be dissolved completely in the conditions of the procedure: a part of insoluble Cocaine base remains in the tube at the first measurement of the solute aliquot.

The second one is that addition of acid (preferably hydrochloric one) to the liquid sample prepared for the first phase, promotes the reaction of protonation of Cocaine base, if it is present in the sample, converting it to hydrochloric salt which is more soluble in the liquid sample (http://www.aapsj.org/view.asp?art=ps050104).

Figure 2:
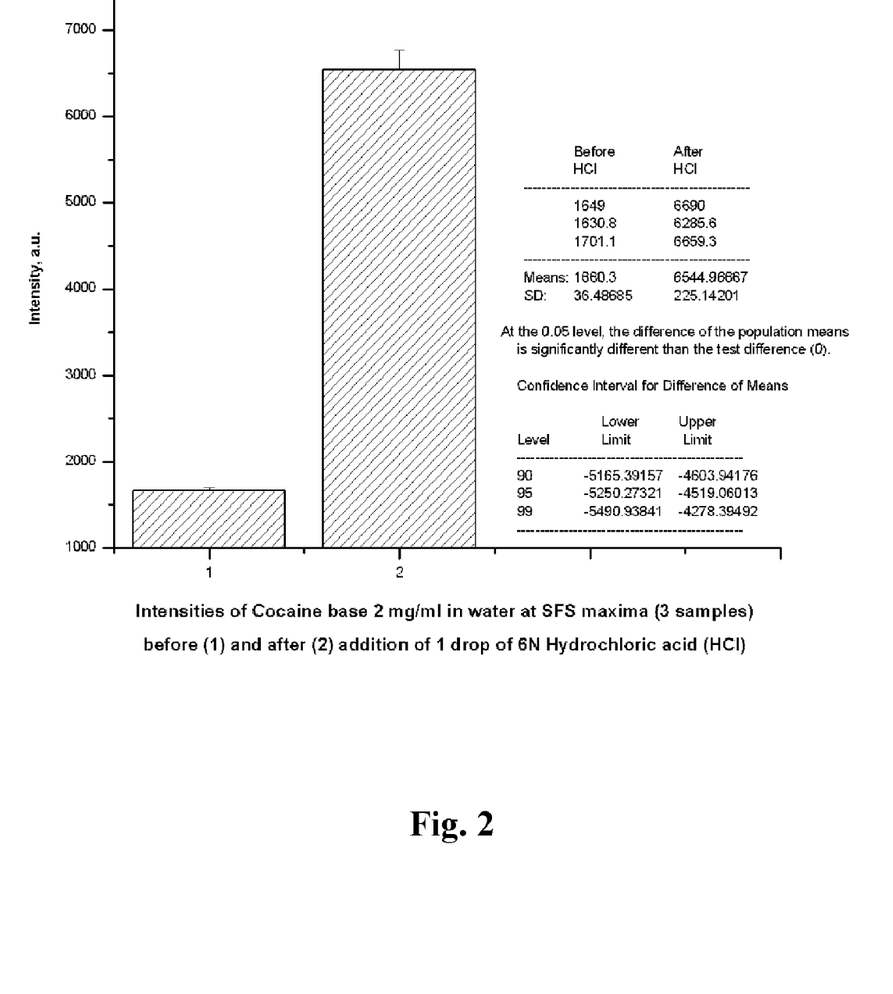
FIG. 2: Increase of fluorescence intensity of Cocaine base in water (2 mg/ml) in two-phase procedure.
Figure 3:
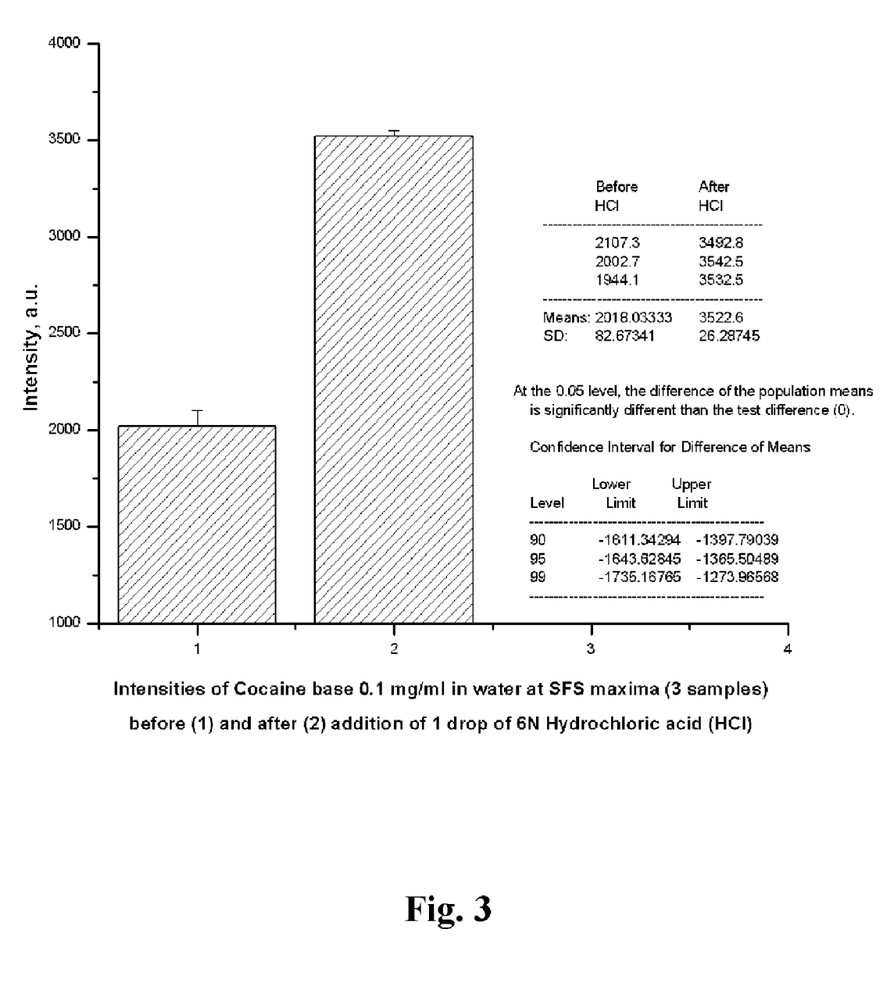
FIG. 3: Increase of fluorescence intensity of Cocaine base in water (0.1 mg/ml) in two-phase procedure.
Figure 4:
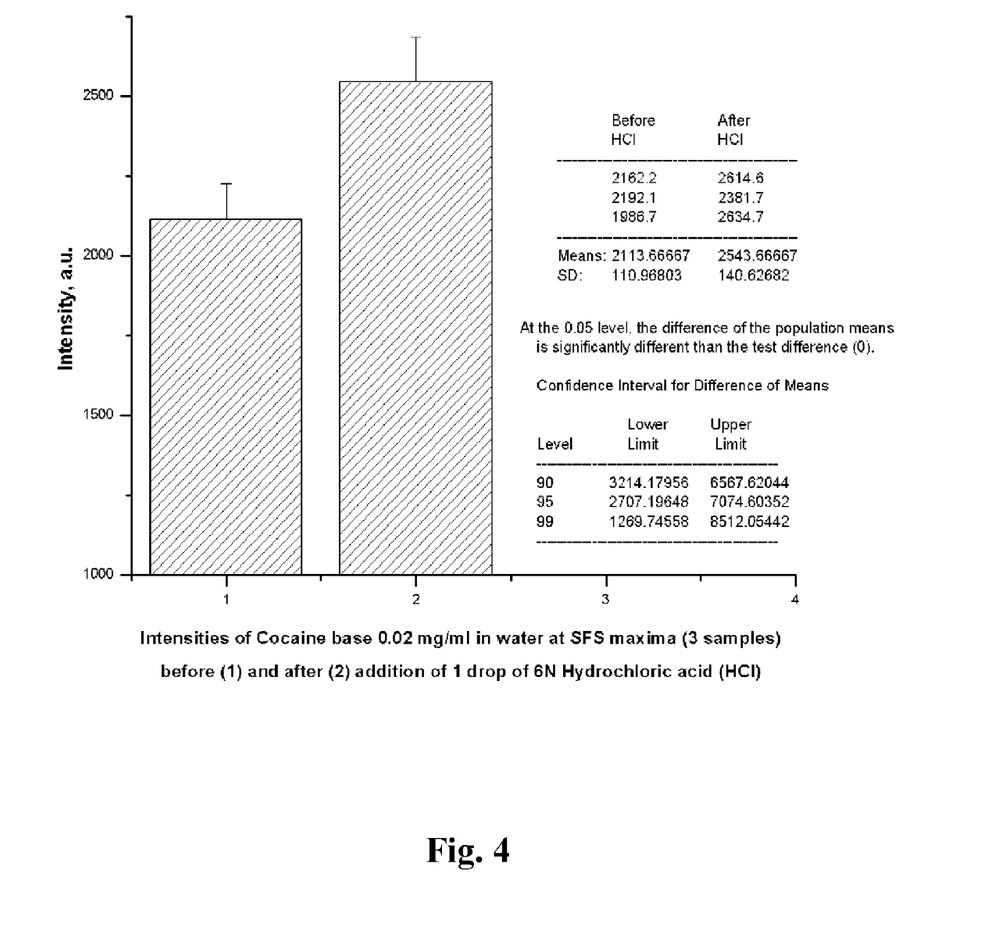
FIG. 4: Increase of fluorescence intensity of Cocaine base (0.02 mg/ml) in two-phase procedure.
Figure 5:
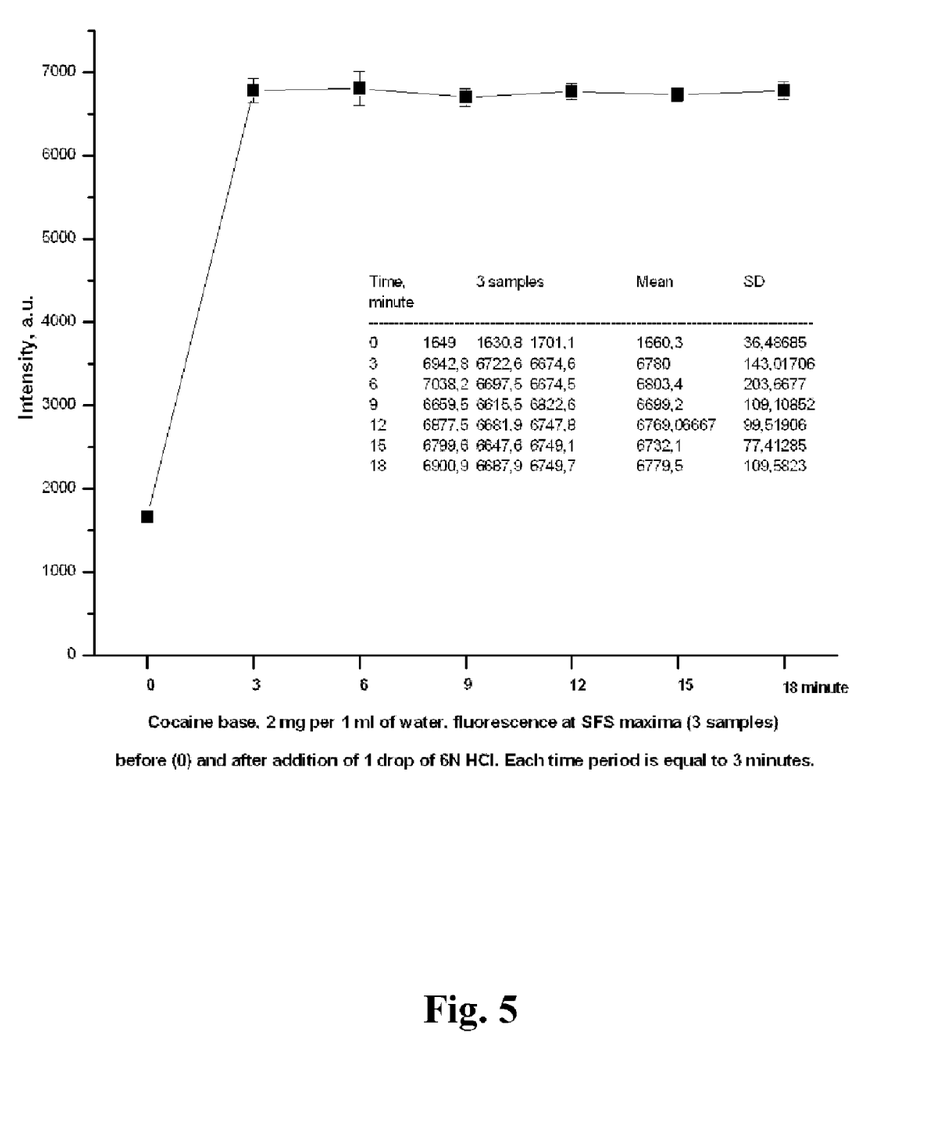
FIG. 5: Time dependency of fluorescence increase of Cocaine base (2 mg/ml) after acidification.
Figure 6:
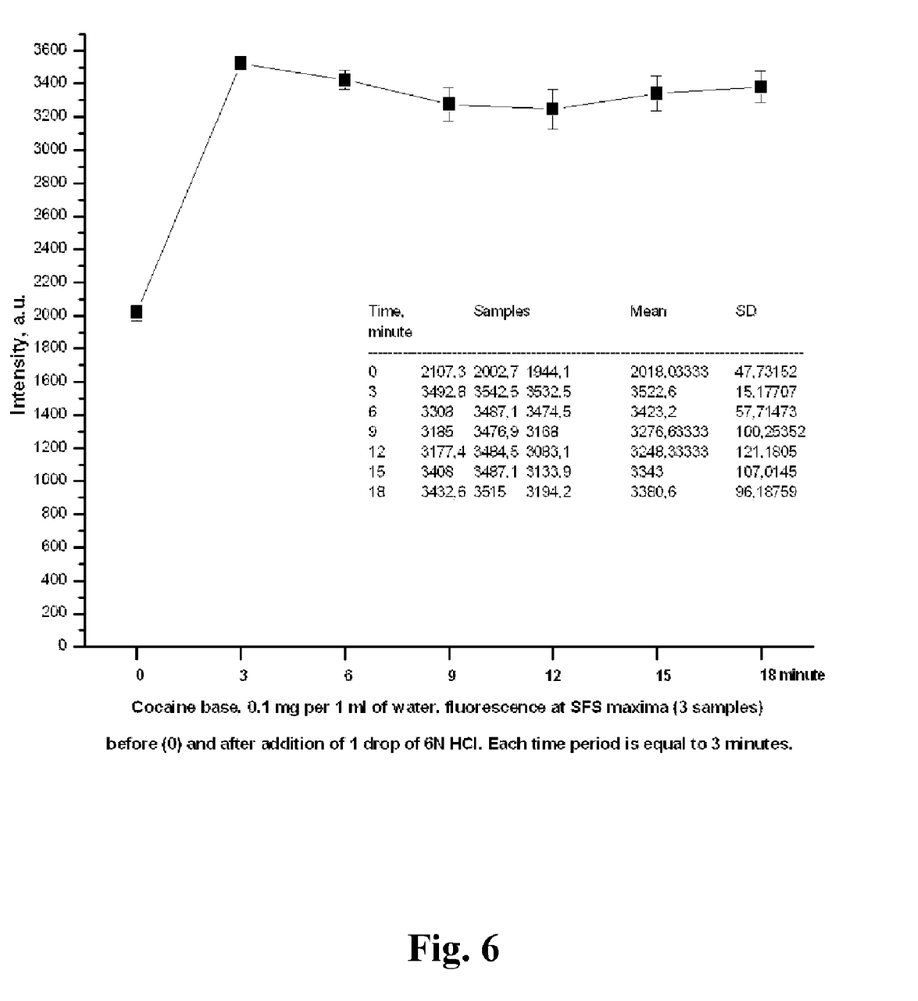
FIG. 6: Time dependency of fluorescence increase of Cocaine base (0.1 mg/ml) after acidification.
Figure 7:
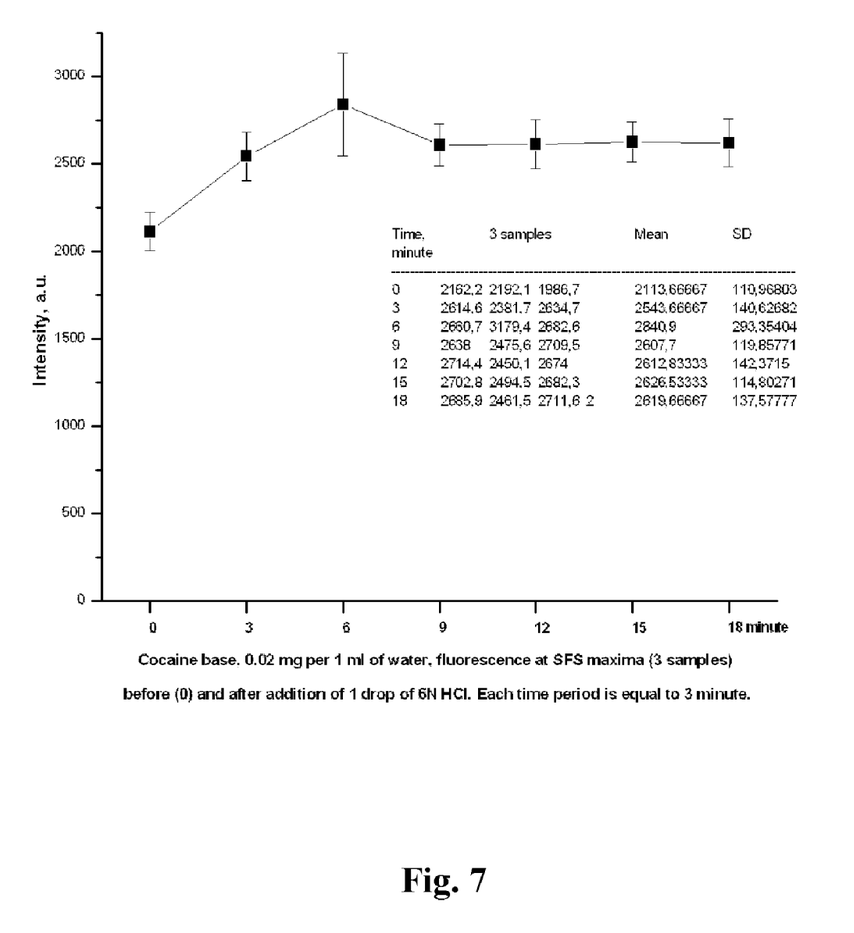
FIG. 7: Time dependency of fluorescence increase of Cocaine base (0.02 mg/ml) after acidification.

As a result of this reaction, more Cocaine becomes soluble, its concentration rises and fluorescence increases. This increase of fluorescence changes the SFS at the second phase of measurement of Cocaine (FIG. 2-4), thus enhancing its easier detection with expert system. FIG. 5-7 show time dependency of protonation process for Cocaine base in acidified sample, indicating that minimal time delay between acidification and measurement by device is about 3 minutes.

Figure 8:
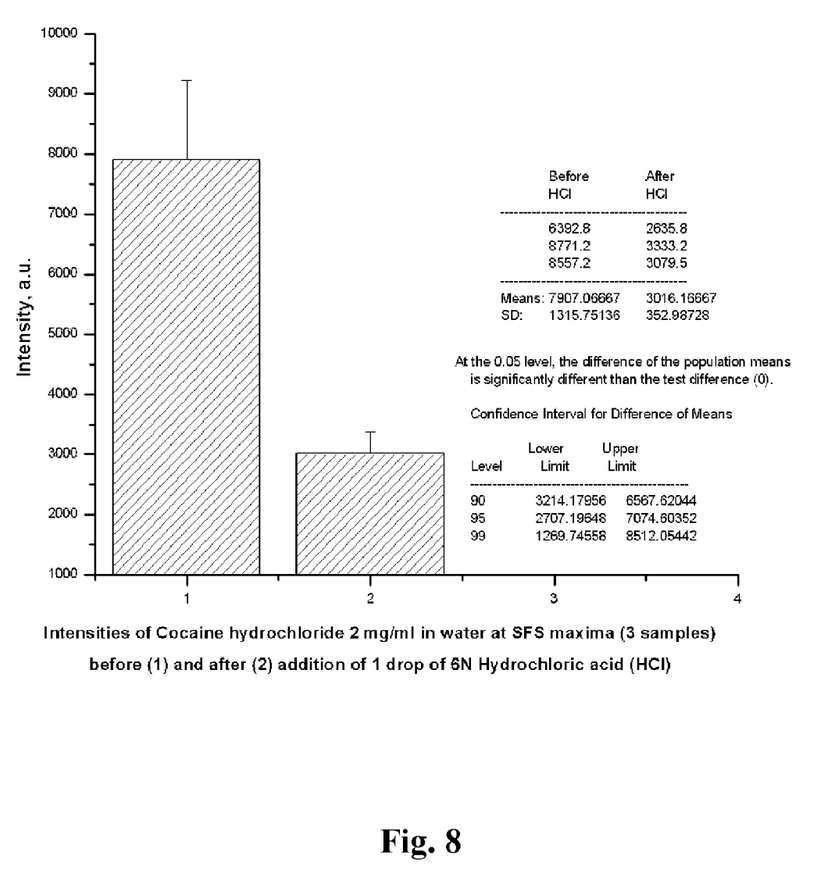
FIG. 8: Fluorescence intensity of Cocaine hydrochloride (2 mg/ml) in two-phase procedure.
Figure 9:
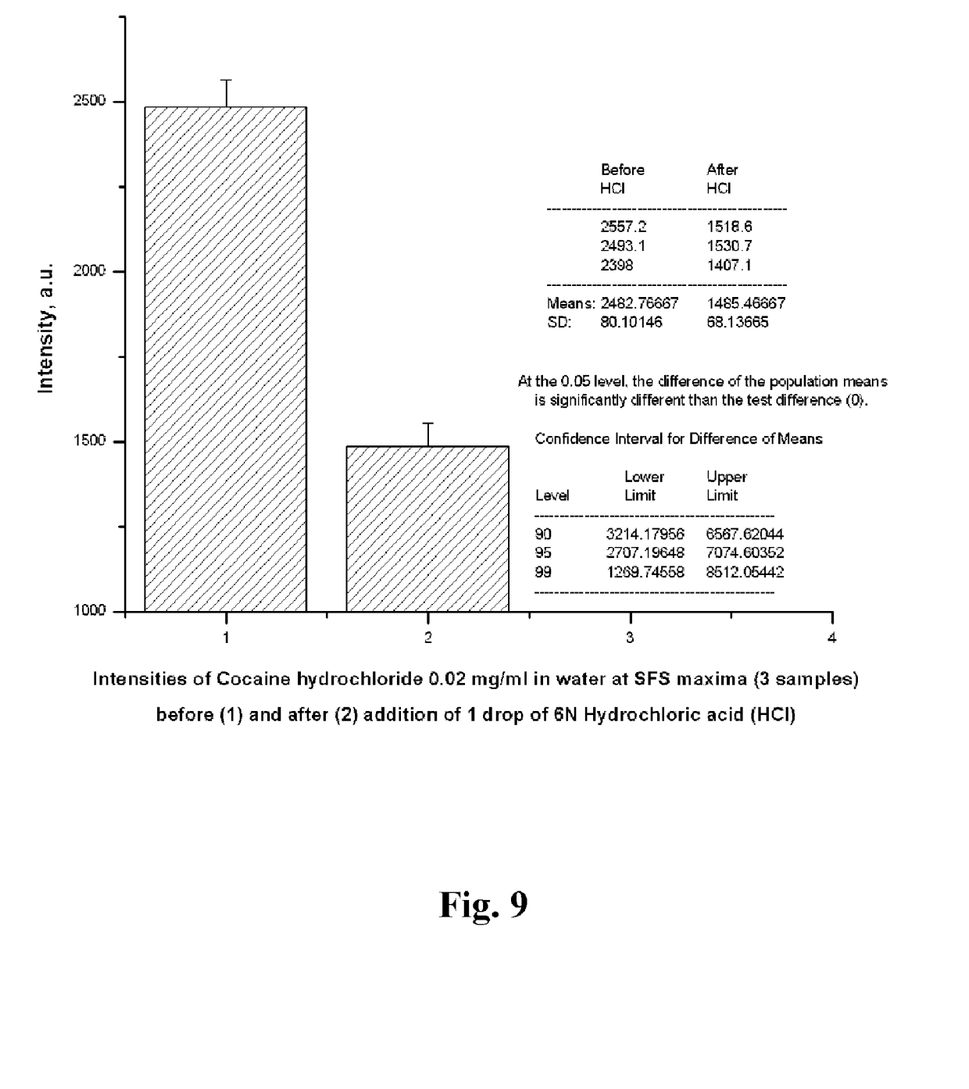
FIG. 9: Fluorescence intensity of Cocaine hydrochloride (0.02 mg/ml) in two-phase procedure.

Addition of acid to the sample containing Cocaine hydrochloride does not lead to the increase of the fluorescence intensity at the corresponding excitation and emission wavelengths. The fluorescence intensity either decreases or remains at the same level. (FIG. 8-9).

After completion of the first phase of analysis the intensity of Cocaine fluorescence in the corresponding spectral pattern of SFS is fixed as a reference value. The second phase analysis is performed by addition of 1-2 drops of hydrochloric acid to the remainder of the liquid sample prepared for the first phase of analysis, taking an aliquot of the acidified liquid sample and re-measuring of it is carried out in the device according to WO2005111586. In principle, it is possible also to use other acids instead of hydrochloric one for acidification of the liquid sample but the hydrochloric acid is preferable due to its comparatively lower harmful properties and low volatile behavior.

After re-measurement the intensity of Cocaine detected at the second phase of analysis—second phase intensity—is compared with the reference value.

If after completion of the second phase of analysis the expert system still does not detect Cocaine in acidified liquid sample, absence of any Cocaine in the street sample is treated as confirmed.

For the liquid sample containing Cocaine base, the second phase intensity will be higher than the reference intensity due to increase of Cocaine concentration in the solute. In opposite, for the liquid samples containing Cocaine hydrochloride, the second phase intensity will be lower than the reference intensity or remain the same (FIG. 8-9). Therefore the second phase of the procedure makes possible the differentiation between Cocaine hydrochloride and Cocaine base.

Table 1 shows the typical change of fluorescence intensity of Cocaine base in different percent concentration fixed by the applicant in experimental laboratory samples.

TABLE 1

| SFS ID number | Cocaine base concentration, % | Fluorescence intensities, a.u. | | Intensity difference, % |
|---|---|---|---|---|
| | | First phase | Second phase | |
| 8187 | 100 | 1470 | 7369 | +401 |
| 8189 | 100 | 1344 | 7250 | +439 |
| 8191 | 100 | 1172 | 7430 | +439 |
| 8193 | 75 | 1161 | 7442 | +541 |
| 8195 | 75 | 1239 | 7465 | +503 |
| 8197 | 75 | 1152 | 7180 | +523 |
| 8199 | 50 | 999 | 7163 | +617 |
| 8201 | 50 | 977 | 7139 | +631 |

TABLE 1-continued

| SFS ID number | Cocaine base concentration, % | Fluorescence intensities, a.u. | | Intensity difference, % |
|---|---|---|---|---|
| | | First phase | Second phase | |
| 8203 | 50 | 982 | 6989 | +612 |
| 8205 | 25 | 701 | 6250 | +792 |
| 8207 | 25 | 779 | 6376 | +718 |
| 8209 | 25 | 726 | 6428 | +785 |
| 8211 | 5 | 427 | 2528 | +492 |
| 8213 | 5 | 399 | 3035 | +661 |
| 8215 | 5 | 462 | 3192 | +591 |
| 8217 | 1 | 212 | 896 | +323 |
| 8219 | 1 | 262 | 1087 | +315 |
| 8221 | 1 | 314 | 1842 | +487 |

Table 2 shows typical change of fluorescence intensity of Cocaine hydrochloride with cutting agents fixed by the applicant in experimental laboratory samples.

TABLE 2

| SFS ID number | Cocaine hydrochloride concentration, % | First phase intensity | Second phase intensity | Intensity difference, % |
|---|---|---|---|---|
| 8223 | 100 | 7799 | 2781 | −64 |
| 8225 | 100 | 7668 | 3130 | −59 |
| 8227 | 100 | 7625 | 3390 | −56 |
| 8229 | 50 | 7590 | 3608 | −52 |
| 8231 | 50 | 7738 | 3416 | −56 |
| 8233 | 50 | 7796 | 3435 | −56 |
| 8235 | 25 | 6617 | 3474 | −48 |
| 8237 | 25 | 6671 | 3515 | −47 |
| 8239 | 25 | 6667 | 3462 | −48 |
| 8241 | 5 | 2748 | 1720 | −37 |
| 8243 | 5 | 2661 | 1580 | −41 |
| 8245 | 5 | 2546 | 1676 | −34 |
| 8247 | 1 | 651 | 469 | −28 |
| 8249 | 1 | 666 | 432 | −35 |
| 8251 | 1 | 642 | 444 | −31 |

The presented above data confirm efficacy of the procedure of sample acidification for Cocaine hydrochloride and Cocaine base reliable detection and their differentiation.

Two-phase analytical procedure provides differentiation between Cocaine hydrochloride and Cocaine base. Significant increase of Cocaine base fluorescence and decrease of Cocaine hydrochloride fluorescence is observed as a result of it. Time dependence of the studied acidification effect demonstrates that approximately 3 minutes is required to provide the changes and further stabilization of the fluorescence intensity.

Increase of fluorescence of Cocaine base after acidification provides also higher sensitivity of the SFS analysis for this form of Cocaine.

A step-by-step performance of the present invention is presented below.
1. Transferring a proper amount of the street sample into a test container with a rational volume of pure water.
2. Giving the amount of street sample to dissolve at possible instant within 3 minute allowing any insoluble materials settle to the bottom of the container.
3. Taking a proper aliquot of the dissolved street sample (liquid sample) and placing it into the measuring cell of the device according to WO2005111586.
4. Measuring the SFS of aliquot and detecting specific spectral pattern of Cocaine. Measuring the intensity of Cocaine fluorescence at the first phase of the two-phase procedure.
5. Acidification of the remainder of the dissolved street sample with possibly non-soluble particles and giving a proper time for non-soluble particles to dissolve in possible degree within at least 3 minutes. Allowing any insoluble materials settle to the bottom of the test container.
6. Taking a proper aliquot of the dissolved acidified street sample and placing it into the measuring cell of the device according to WO2005111586.
7. Measuring the SFS of acidified aliquot and detecting specific spectral pattern of Cocaine. Measuring the intensity of Cocaine fluorescence at the second phase of two-phase procedure.
8. Comparing the intensities of Cocaine fluorescence at the first phase and second phase of the two-phase procedure provided that the intensity of Cocaine fluorescence at the first phase is detected. Higher intensity at the second phase indicates that Cocaine base is present in the street sample. And on the contrary, lower or unchanged intensity at the second phase indicates that Cocaine hydrochloride is present in the street sample. Absence of Cocaine fluorescence at the both phases indicates that neither Cocaine base nor Cocaine hydrochloride are present in the street sample.

The working range for the detection and differentiation is from 5% till 100% of cocaine in the sample. According to the procedure it is equal to 1 mg-20 mg per 10 ml of water. The real lowest level of cocaine detection in street samples is about 1% or 0.2 mg per 10 ml of water. Intensity of cocaine fluorescence depends on its concentration in this range.

The procedure of Cocaine base detection and differentiation from Cocaine hydrochloride can be provided automatically by Expert system analyzing the SFS. Such expert system considers not only the shape and position of Cocaine spectra but their intensities in parallel: appearance of Cocaine spectral pattern or increase of its fluorescence intensity after acidification of the measuring sample is used as the evidence of Cocaine base property of the detected Cocaine.

The data below demonstrate increase of SFS intensity of Cocaine base and decrease of SFS intensity of Cocaine hydrochloride after acidification of their solutes in distilled water. Study of time dependence of these changes supplements the stated changes.

Table 3 shows application of two-phase analytical procedure for differentiation of Cocaine base and cocaine hydrochloride fixed by the applicant in experimental laboratory samples.

TABLE 3

| SFS ID number | Fluorescence intensities, a.u. | | Intensity difference, % | Result |
|---|---|---|---|---|
| | First phase | Second phase | | |
| 8223 | 653.12 | 2501.45 | +283 | Cocaine base |
| 8225 | 475.58 | 4603.54 | +868 | Cocaine base |
| 227 | 753.54 | 5809.56 | +671 | Cocaine base |
| 8229 | 7449.36 | 6234.73 | −16 | Cocaine hydrochloride |
| 8231 | 284.46 | 239.7 | −16 | Cocaine hydrochloride |
| 8233 | 4099.25 | 2056.85 | −50 | Cocaine hydrochloride |
| 8235 | 5308.69 | 4927.63 | −7 | Cocaine hydrochloride |
| 8237 | 5441.14 | 5216.5 | −4 | Cocaine hydrochloride |
| 8239 | 774.64 | 4538.06 | +486 | Cocaine base |
| 8241 | 769.19 | 6710.65 | +772 | Cocaine base |
| 8243 | 426.75 | 5053.65 | +1084 | Cocaine base |
| 8245 | 6011.37 | 4887.47 | −19 | Cocaine hydrochloride |
| 8247 | 806.53 | 6293.99 | +680 | Cocaine base |

TABLE 3-continued

| SFS ID number | Fluorescence intensities, a.u. | | Intensity difference, % | Result |
|---|---|---|---|---|
| | First phase | Second phase | | |
| 8249 | 6890.81 | 5584.47 | −19 | Cocaine hydrochloride |
| 8251 | 6831.84 | 5908.92 | −14 | Cocaine hydrochloride |

The disclosed embodiment of the invention does not determine its scope of protection, but shows only one of variants of its realization within the scope defined by claims.

The invention claimed is:

1. Method for drug detection in a drug sample comprising the steps of:
   a) preparing a liquid sample from a drug sample for analysis;
   b) introducing an aliquot of a liquid sample of the drug into a measuring cell of a Spectral Fluorescence Signatures (SFS) device;
   c) measuring the SFS of the aliquot liquid sample to obtain a reference value of SFS;
   d) adding acid into the liquid sample;
   e) introducing the acidified aliquot liquid sample into the measuring cell of the SFS device;
   f) measuring the SFS of the acidified aliquot liquid sample; and
   g) comparing the reference value and the result of the measurement of SFS of the acidified aliquot liquid sample, wherein if:
      i) the SFS of the acidified aliquot liquid sample exceeds the reference value Cocaine base is present in the drug sample
      ii) SFS of the acidified aliquot liquid sample is below the reference value or is equal to the reference value, and the reference value is not zero, Cocaine hydrochloride is present in the drug sample; and
      iii) the SFS of the acidified aliquot liquid sample equals the reference value and the reference value is zero, Cocaine is not present in the drug sample.

2. The method according to claim 1, wherein the liquid sample is prepared by dissolving a dry sample of the drug in purified water.

3. The method according to claim 2, wherein the purified water is distilled water.

4. The method according to claim 1, wherein the amount of acid added into the liquid sample is 1 to 2 drops.

5. The method according to claim 1, wherein the SFS is not measured for at least 3 minutes after adding the acid in step d).

6. The method according to claim 1, wherein the acid is hydrochloric acid.

7. The method according to claim 1, wherein the drug sample is a street sample.

8. The method according to claim 1, wherein the method is carried out on-site.

9. The method according to claim 1, wherein the drug sample is suspected to contain an illegal drug.

* * * * *